United States Patent [19]

Searfoss et al.

[11] Patent Number: 5,046,494
[45] Date of Patent: Sep. 10, 1991

[54] PHOTOTHERAPY METHOD

[76] Inventors: John Searfoss, 70 E. Arrow, Box 70, Marshall, Mo. 65340; Robert L. Searfoss, III, 1370-3 Chalmette Dr. NE., Atlanta, Ga. 30306

[21] Appl. No.: 573,531
[22] Filed: Aug. 27, 1990
[51] Int. Cl.$^5$ ............................................. A61N 5/06
[52] U.S. Cl. ................................. 128/395; 128/380; 600/27
[58] Field of Search .............................. 128/395–398, 128/380; 600/26, 27

[56] References Cited

U.S. PATENT DOCUMENTS

| | | | |
|---|---|---|---|
| 3,326,204 | 6/1967 | Fratiel et al. | 600/27 |
| 4,858,609 | 8/1989 | Cole | 128/395 |
| 4,892,106 | 1/1990 | Gleeson, III | 128/395 |

FOREIGN PATENT DOCUMENTS 3447105  7/1985  Fed. Rep. of Germany ........ 600/27

Primary Examiner—Edward M. Coven
Assistant Examiner—Mark S. Graham
Attorney, Agent, or Firm—Fulwider, Patton, Lee & Utecht

[57] ABSTRACT

An method for displaying to an observer a field of light, controllably variable in terms of color, size and intensity and a method of varying the color, size and intensity of the field of light in order to achieve a therapeutic effect in the observer. The field of light is displayed first at a long wavelength, low intensity small area, and slow pulse rate, and then at a relatively short wavelength, high intensity large area, and high pulse rate.

2 Claims, 1 Drawing Sheet

PHOTOTHERAPY METHOD

BACKGROUND OF THE INVENTION

1. Field of the Invention

This invention relates to phototherapy and more particularly pertains to a method and apparatus for exposing an observer to a precisely controlled display of light in order to achieve a therapeutic effect.

2. Description of the Prior Art

It has long been recognized that light can have profound psychological as well as physiological effects on the human organism. Although both ocular as well as non-ocular techniques have been employed in an attempt to achieve various such effects, ocular treatment appears to be most efficacious. Not only are the eyes highly specialized organs specifically adapted for sensing light, but a sizable portion of the brain is exclusively devoted to processing data generated by the retinas. Moreover, neurologists and anatomists have relatively recently demonstrated the existence of nerve pathways extending from the retinas that are separate and apart from the pathways linked to the sight center of the brain. These newly discovered interconnections link the eyes with neurological centers in the brain that influence and control many of the body's regulatory functions. Such regulatory centers typically exert their control via neurological or biochemical means.

An example of an organ whose regulatory function is responsive to light sensed by the eyes is the pineal gland which secretes the hormone melatonin. The hormone is released during periods of darkness while production is abruptly halted when the eyes perceive bright light. Melatonin is distributed throughout the body via the blood and cerebrospinal fluid and can effect the function of organs by which it is metabolized to thereby influence sleep cycles, feeding cycles, reproduction cycles and other biological rhythms. It has therefore been suggested that phototherapy may effectively be employed to correct a melatonin imbalance which may have resulted from, for example, shift work, jet lag or life in the polar regions, and thereby remedy the accompanying symptoms.

Other such relationships have been discovered, more are suspected and even more may, in fact, exist. Additionally, it has been found that some of the body's responses to light are acutely dependent upon specific characteristics of the light perceived by the eyes such as the light's wavelength, and intensity, and further, that particular responses can be elicited or enhanced by varying such characteristics according to certain sequences or patterns. Although instruments have been constructed and techniques devised to generally exploit this systemic sensitivity to light, many important factors had not been taken into consideration as required in order to take fuller advantage of the effect of light on the human organism. The present invention seeks to overcome some of these shortcomings.

SUMMARY OF THE INVENTION

This invention provides methods, for more efficaciously utilizing light in order to achieve a therapeutic effect in an observer. Additionally, the invention provides an instrument to enable those methods to be applied.

The apparatus of the present invention provides a means for displaying to an observer a field of light which can be varied in color, size, intensity and illumination duration according to a preselected sequence. Most importantly, in order to minimize distraction and take full advantage of the human being's acute sensitivity to light, it has been found essential to employ a non-oscillating light source and to have the ability to segregate well defined band widths of wavelengths therefrom to the substantial exclusion of all other wavelengths. In a preferred embodiment, light emitted by an incandescent light source powered by a direct current power supply, is passed through a selected one of a plurality of highly selective filters, through a diffuser, and through a selected one of a plurality of apertures positioned so as to be visible to the observer. Filter selection and aperture selection is achieved by rotating a filter disc containing the plurality of different filters thereon and an aperture disc accommodating the plurality of different sized apertures thereon into positions so as to align the light source, the selected filter and the selected aperture with the field of view of the observer. A controller regulates the current supplied to the light source and actuates the servo motors that rotate the filter disc and aperture disc into position.

In an alternate embodiment, two separately controllable light sources are disposed to shine through two separately positionable filter discs to illuminate a common diffuser or integrating sphere visible to the observer through an aperture. This configuration enables a smooth transition from one color to another color to be accomplished and additionally allows two colors to be blended. In another alternate embodiment, two separately controllable light sources are disposed to shine through two separately positionable filter discs to illuminate separate diffusers and shine through two separately controllable aperture discs to provide two separate images, one to each eye. This configuration enables the apparatus to alternately provide monocular, biocular and binocular displays.

A method according to the present invention calls for an individual, otherwise isolated from extraneous sensory input, to undergo a plurality of sessions in which light pulses of controlled color, image size, intensity and duration are displayed in a generally energy-increasing sequence. After a preliminary acclimatization routine, the observer is subjected to a pulsing field of light that gradually progresses from a long wavelength, small size, low intensity, and low pulse rate to a short wavelength, large size, high intensity, and high pulse rate over a period of about 30 minutes. At the end of such a progression, the observer is subjected to a field of light of intermediate size and intensity of a band of wavelengths selected from the middle of the visible spectrum, for a short period of time in order to achieve a "stabilizing" effect. It has been found that a properly receptive observer ultimately perceives a general feeling of well being, accompanied by, or perhaps as a result of, a normalization of vital signs, such as blood pressure, respiration and heart rate, a normalization of blood chemistry including the electrolyte balance, a reduction of local and systemic edema, a normalization of intra-ocular pressure, and stimulation and regulation of hormonal levels, a balancing of the sympathetic and parasympathetic nervous systems and a stimulation of the immune system. Additionally, an increased peripheral awareness, stabilization of the observer's emotions, an increase in psychological awareness, mental clarity and concentration as well as an increase in the efficiency of motor coordination has been observed.

Due to the fact that individual responses differ and that, in fact, certain individuals may favor a particular wavelength, image size, intensity or pulse rate, an alternate method is provided herein to take advantage of this phenomenon. In an alterative method, observer feedback is relied upon to identify those values of the various parameters that have the most effect, one parameter at a time. Initially, a single parameter is varied and the observer is asked which value appears the have the most soothing effect. In subsequent sessions, the parameters for which favored values have been identified are held constant while other parameters are varied until all parameters are optimized for a particular individual. The above-described therapeutic effects can then repeatedly be realized during relatively short sessions in which the observer is subjected to an individualized light display wherein the parameters to which he is most responsive are held constant. At the end of each such session, the observer is "stabilized" by subjection to a band of light frequencies selected from the middle of the visible spectrum, of intermediate image size and intensity.

Other features and advantages of the present invention will become apparent from the following detailed description, taken in conjunction with the accompanying drawings, which illustrate by way of example, the principles of the invention.

DETAILED DESCRIPTION OF THE INVENTION

Figure 1:
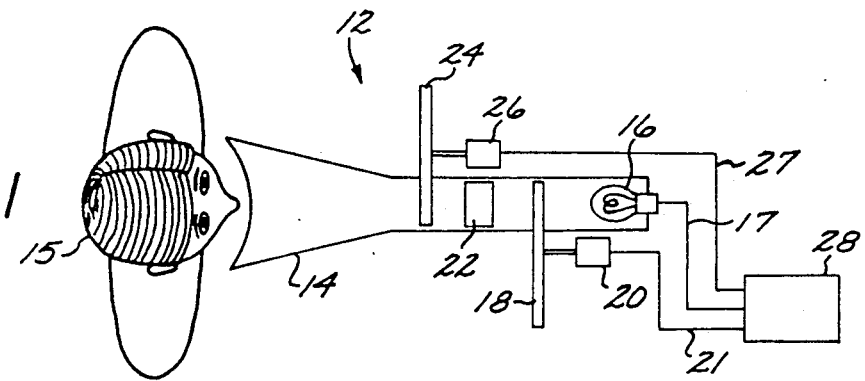
FIG. 1 is a partially schematic representation of an embodiment of the present invention.
Figure 2:
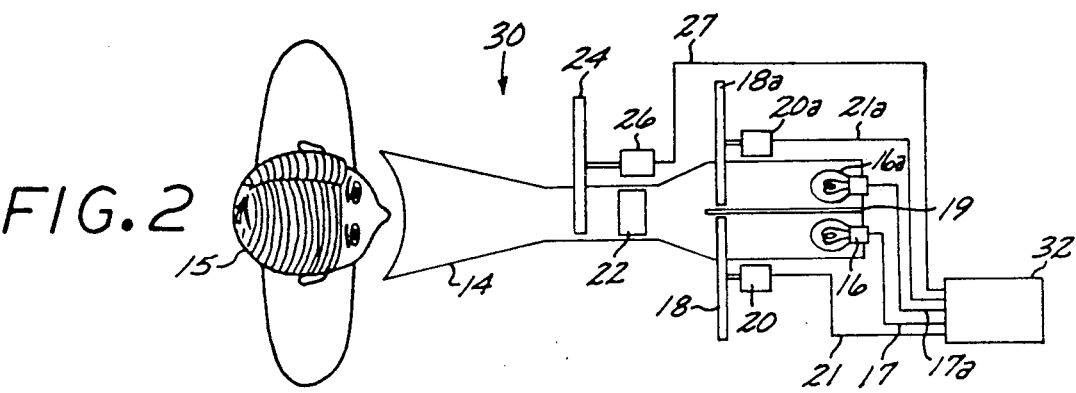
FIG. 2 is a partially schematic representation of an alternate embodiment of the present invention.
Figure 3:
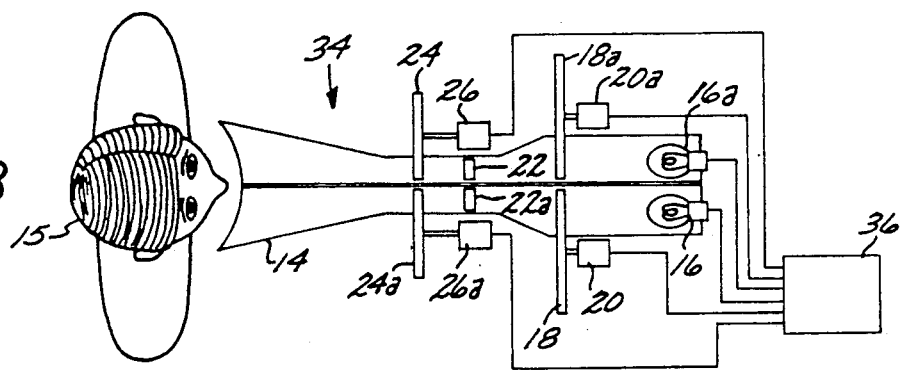
FIG. 3 is a partially schematic representation of another alternate embodiment of the present invention.

FIGS. 1-3 generally illustrate embodiments of the present invention with which the methods of the present invention are practiced. An apparatus according to the present invention provides a display of light to an observer peering thereinto. Various parameters of the light display can be varied, sequenced and optimized so as to render a therapeutic effect in the observer.

FIG. 1 illustrates a preferred embodiment of the invention. The phototherapy apparatus 12 has a hooded section 14 configured and positioned such that an observer 15 can comfortably gaze thereinto. A light source 16 is placed at the opposite end of the device. The light source 16 preferably consists of an incandescent light bulb powered by direct current to thereby emit a constant non-oscillating flux of light. It has been found that the cyclical variation in intensity of an AC powered light source is readily discerned subconsciously and can prove distracting. The power is supplied from within controller 28 via conduit 17. Means are provided for varying and precisely controlling the amount of power supplied.

It is then necessary to segregate very "pure" colors from the light emitted by source 16. For the purposes of the present invention, the purity of color pertains to the frequency distribution of the segregated light. Each color includes continuum of approximately one eighth of the frequencies of the visible spectrum, with a very sharp cutoff at the high energy and low energy extremes of the desired band. Light refracted by a rotatable prism provides the requisite band definition. The use of commercially available highly selective filters comprises the preferred manner of achieving the required purity of color.

Figure 4:
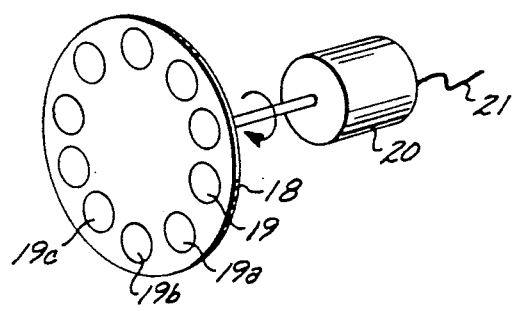
FIG. 4 is a perspective view of a component of the embodiments illustrated in FIGS. 1-3.
Figure 5:
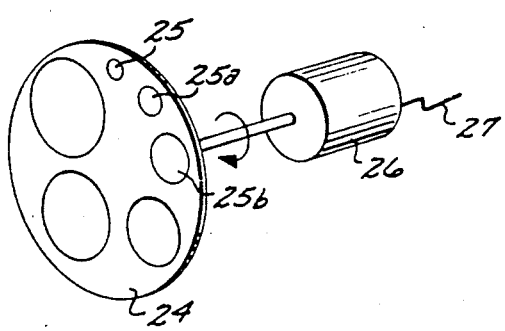
FIG. 5 is a perspective view of another component of the embodiments illustrated in FIGS. 1-3.

FIG. 4 illustrates a filter disc 18 in which eight different filters 19, 19a, 19b, etc. are accommodated, each corresponding to a different color in the visible spectrum. Servo motor 20 rotates disc 18 as per a signal issued by controller 28 via conduit 21 to position a selected filter directly in front of the light source 16.

Light passing through the selected filter is subsequently diffused in diffuser 22. While a ground glass plate is preferred, an integrating sphere can be used to achieve the required homogeneous field of light.

The diffused light then passes through a selected one of a number of apertures 25, 25a, 25b, etc. A plurality of different size apertures are accommodated on the single aperture disc 24 which is rotatable by servo motor 26 which in turn is controllable via a signal from controller 28 conducted through conduit 27. An assortment of apertures would increase the amount of light transmitted from the smallest area to an area for example 2×, 4×, 8×, to 10×, etc. as large.

By controlling the amount of current supplied to light source 16, the position of filter disc 18 and the position of aperture disc 24, a field of light can be displayed to the observer 15 with a precisely controlled size, intensity and color.

FIG. 2 illustrates a modified version of the device illustrated in FIG. 1. An additional light source 16a shines through an additional filter disc 18a onto common diffuser 22. A partition 19 segregates the two light sources 16 and 16a and the two filter discs 18 and 18a. A second servo motor 20a drives filter disc 18a. Controller 32 is capable of individually controlling the current conducted to the two light sources 16, 16a and additionally has the capability of individually controlling the position of filter discs 18 and 18a.

FIG. 3 illustrates a modified version of the embodiment illustrated in FIGS. 1 and 2. The device essentially comprises two phototherapy apparatus 12 illustrated in FIG. 1 arranged in parallel such that the light displayed to each eye of observer 15 is individually controllable in terms of color, size and intensity. A partition 23 extending up to observer 15 ensures that the right eye cannot see what the left eye sees and vice versa. Controller 36 is capable of individually controlling current conducted to the two light sources 16 and 16a, is capable of individually controlling the position of the two filter discs 18 and 18a via their respective servo motors 20 and 20a and is additionally capable of individually controlling the position of the aperture discs 24 and 24a via their respective servo motors 26 and 26a.

A method by which the apparatus of the present invention is utilized to achieve a therapeutic effect in an observer consists of providing to the observer a sequence of light displays varying in terms of size, wavelength, pulse rate, and intensity in a generally energy increasing pattern. The size of the field of light is gradually increased, the wavelength is gradually decreased, the pulse rate is gradually increased, while the maximum intensity of the pulses is also gradually increased. The effectiveness of such therapy sessions is enhanced by isolating the observer from distractions, such as extraneous light and sound and minimizing postural stresses thereby allowing the individual to properly concentrate on the light display provided by the apparatus of the present invention. At the end of the progression of light displays to which the observer is subjected, a field of light of frequencies selected from the middle of the visible spectrum, such as green, of intermediate size and intensity is displayed to the observer for a short period of time for a stabilizing effect.

Sessions in which the observer is subjected to such energy-increasing displays are repeated to enable the observer to become cognizant of his body's response to the light display. By either objectively monitoring such physiological responses such as heart rate, respiration rate, blood pressure, galvanic skin response, muscle tension, intraocular pressure, brain wave shift toward theta waves produced by the brain, body temperature, ocular tear secretion rate or motion activity, or alternatively, relying on the observer's subjective observations, an optimum wavelength, pulse rate, field size, intensity combination or combination range can be identified which appears to have the most effect. Continued exposure to light having those particular characteristics can bring about physiological or psychological changes of therapeutic value. Immediately after each such exposure, the observer is subjected to a field of light of intermediate size and intensity and of a color from the middle of the visible spectrum to achieve a stabilizing effect.

While a particular form of the invention has been illustrated and described, it will also be apparent to those skilled in the art that various modifications can be made both to the apparatus as well as to the methods employed without departing from the spirit and scope of the invention. Accordingly it is not intended that the invention be limited except as by the appended claims.

What is claimed is:

1. A method for achieving a therapeutic effect in an observer, comprising the steps of directing towards said observer's eyes a pulsing field of light controllable in terms of wavelength, intensity, area, and pulse rate in a sequence commencing with a relatively long wavelength, low intensity, small area and slow pulse rate and progressing to a light field of relatively short wavelength, high intensity, large area, and high pulse rate.

2. The method of claim 1 further comprising the step of displaying to said observer immediately after said sequence, a field of light of intermediate wavelength, area and intensity.

* * * * *